US009546353B2

(12) United States Patent
Ganchas Soares et al.

(10) Patent No.: US 9,546,353 B2
(45) Date of Patent: Jan. 17, 2017

(54) OPTIMIZED AND DEFINED METHOD FOR ISOLATION AND PRESERVATION OF PRECURSOR CELLS FROM HUMAN UMBILICAL CORD

(75) Inventors: Rita Isabel Ganchas Soares, Oeiras (PT); Maria Constança Baptista Coelho, Oeiras (PT); Jorge Miguel Silva Santos, Oeiras (PT); José Paulo Martins, Oeiras (PT); Vera Alexandra Basto, Oeiras (PT); Pedro Estilita Monteiro Da Cruz, Oeiras (PT); Helder Joaquim Soares Da Cruz, Oeiras (PT)

(73) Assignee: Laboratorio Medinfar-Produtos Farmaceuticos, S.A., Amadora (PT)

( * ) Notice: Subject to any disclaimer, the term of this patent is extended or adjusted under 35 U.S.C. 154(b) by 775 days.

(21) Appl. No.: 12/680,604

(22) PCT Filed: Oct. 3, 2008

(86) PCT No.: PCT/IB2008/054067
§ 371 (c)(1),
(2), (4) Date: Mar. 29, 2010

(87) PCT Pub. No.: WO2009/044379
PCT Pub. Date: Apr. 9, 2009

(65) Prior Publication Data
US 2010/0216237 A1    Aug. 26, 2010

(30) Foreign Application Priority Data
Oct. 4, 2007   (PT) .......................................... 103843

(51) Int. Cl.
*C12N 5/073*    (2010.01)
*C12N 5/0775*   (2010.01)

(52) U.S. Cl.
CPC ........... *C12N 5/0605* (2013.01); *C12N 5/0668* (2013.01); *C12N 2509/00* (2013.01)

(58) Field of Classification Search
None
See application file for complete search history.

(56) References Cited

U.S. PATENT DOCUMENTS 5,770,578 A  *  6/1998  Binder et al. ................... 514/26

OTHER PUBLICATIONS

Jeschke MG et al. 2011. Umbilical Cord Lining Membrane and Wharton's Jelly-Derived Mesenchymal Stem Cells: the Similarities and DifferencesThe Open Tissue Engineering and Regenerative Medicine Journal 4: 21-27.*
Mitchell KE et al. 2003. Matrix cells from Wharton's jelly form neurons and glia. Stem Cells 21: 50-60.*
Weiss ML et al. 2006. Stem cells in the umbilical cord. Stem Cell Rev 2: 155-162.*
van de Ven C et al. 2007. The potential of umbilical cord blood multipotent stem cells for nonhematopoietic tissue and cell regeneration. Exp Hematol 35: 1753-1765.*
Mark L. Weiss et al. "Human Umbilical Cord Matrix Stem Cells: Preliminary Characterization and Effect of Transplantation in a Rodent Model of Parkinson's Disease"; Stem Cells; vol. 24., No. 3. pp. 781-792 (Mar. 2006); XP002463574.
Alp Can et al. "Concise Review: Human Umbilical Cord Stroma with Regard to the Source of Fetus-Derived Stem Cells"; Stem Cells; vol. 25., No. 11. pp. 2886-2895 (Aug. 2007); XP002521370.
Lu-lu Lu et al. "Isolation and characterization of human umbilical cord mesenchymal stem cells with hematopoiesis-supportive function and other potentials"; Haematologica, Fondazione Ferrata Storti; vol. 91, No. 8. pp. 1017-1026 (Aug. 2006); XP009110905.
International Search Report for PCT/IB2008/054067 dated Apr. 9, 2009.
Barry, "Mesenchymal Stem Cells: Clinical Applications and Biological Characterization," International Journal of Biochemistry and Cell Biology, vol. 36, No. 4, pp. 568-584, 2004.
Hung et al., "Isolation and Characterization of Size-Sieved Stem Cells From Human Bone Marrow," Stem Cells, vol. 20, No. 3, pp. 249-258, 2002.
Kadner et al., "Human Umbilical Cord Cells for Cardiovascular Tissue Engineering: A Comparative Study," European Journal of Cardio-Thoracic Surgery, vol. 25, No. 4, pp. 635-641, 2004.
Kotobuki et al., "Observation and Quantitative Analysis of Rat Bone Marrow Stromal Cells Cultured In Vitro on Newly Formed Transparent β-Tricalcium Phosphate," Journal of Materials Science: Materials in Medicine, vol. 17, No. 1, pp. 33-41, 2006.
Majumdar et al., "Phenotypic and Functional Comparison of Cultures of Marrow-Derived Mesenchymal Stem Cells (MSCs) and Stromal Cells," Journal of Cellular Physiology, vol. 176, No. 1, pp. 57-66, 1998.
Nanaev et al., "Stromal Differentiation and Architecture of the Human Umbilical Cord," Placenta, vol. 18, No. 1, pp. 53-64, 1997.
Pittenger et al., "Multilineage Potential of Adult Human Mesenchymal Stem Cells," Science, vol. 284, No. 5411, pp. 143-147, 1999.

(Continued)

*Primary Examiner* — Suzanne M Noakes
*Assistant Examiner* — Stephen Chong
(74) *Attorney, Agent, or Firm* — Margaret B. Brivanlou; Nicole Fortune; King & Spalding LLP

(57) ABSTRACT

The present invention refers to an optimized and defined method for isolation and preservation of precursor cells from human umbilical cord. Besides being reproducible and 100% reliable, in terms of the number of samples processed, the method results in a high and defined number of precursor cells, being the majority obtained after a single adhesion and expansion/multiplication phase ex vivo (thus granting cell phenotype), in a shorter time frame than what was previously described in the state-of-the-art. With this method, it is possible to obtain, in 9 days, after direct freezing of a cell fraction, and after one expansion/multiplication phase ex vivo (end of P0) of the majority of the cells, about 8.6 ($\pm$0.1)$\times 10^5$ cells/gram of processed umbilical cord. In turn, the characteristics of the cells allow, for example, after 35 days, obtaining an average of $7.7 \times 10^{15}$ cells, with precursor phenotype, from 100% of processed umbilical cord samples. The method, because it is simple, robust and 100% reliable, can be performed under good manufacturing practices (GMP) in laboratories dedicated to cell therapy in humans. Furthermore, the method has applications in the pharmaceutical, cosmetic and biotechnology areas.

19 Claims, 7 Drawing Sheets

(56) References Cited

OTHER PUBLICATIONS

Roisen et al., "Adult Human Olfactory Stem Cells," Brain Research, vol. 890, No. 1, pp. 11-22, 2001.
Romanov et al., "Searching for Alternative Sources of Postnatal Human Mesenchymal Stem Cells: Candidate MSC-Like Cells From Umbilical Cord," Stem Cells, vol. 21, No. 1, pp. 105-110, 2003.
Shih et al., "Isolation and Characterization of Neurogenic Mesenchymal Stem Cells in Human Scalp Tissue," Stem Cells, vol. 23, pp. 1012-1020, 2005.
Shim et al., "Ex vivo Differentiation of Human Adult Bone Marrow Stem Cells Into Cardiomyocyte-Like Cells," Biochemical and Biophysical Research Communications, vol. 324, No. 2, pp. 481-488, 2004.
Troyer, "Concise Review: Wharton's Jelly-Derived Cells Are a Primitive Stromal Cell Population," Stem Cells, vol. 26, No. 3, pp. 591-599, 2008.

\* cited by examiner

A.

B.

OPTIMIZED AND DEFINED METHOD FOR ISOLATION AND PRESERVATION OF PRECURSOR CELLS FROM HUMAN UMBILICAL CORD

TECHNICAL FIELD OF THE INVENTION

This application is a U.S. national phase filing under 35 U.S.C. §371 of PCT Application No. PCT/IB2008/054067, filed Oct. 3, 2008, and claims priority thereto under 35 U.S.C. §119 to Portuguese patent application no. 103843, filed Oct. 4, 2007, the entireties of both of which are incorporated by reference herein.

It is an aspect of the present invention an optimized and defined method for isolation and preservation of precursor cells from the human umbilical cord matrix.

By "precursor cell" in the present invention, it is meant a type of cell capable of adhering and expanding/multiplying in a surface and defined growth medium, where the majority of cells in culture express the cell surface markers CD44, CD73, CD90 and CD105, and the majority of cells present only residual expression of the cell surface markers CD14, CD31, CD34 and CD45, where the majority of cells are able to undergo up to 18 expansion/multiplication phases, maintaining a constant duplication factor of approximately 1.7/24 h, a constant fibroblast-like morphology, and the capacity of partial or terminal differentiation into specialized cells, such as osteoblasts, chondrocytes, adipocytes, cardiomyocytes, and glial/neural cells.

An aspect of the present invention adds to the state-of-the-art a method which is robust, allowing 100% efficacy related to the tissue samples processed, and more efficient, related to the number of stem cells isolated per umbilical cord mass and dispended time.

The technical innovations that are the basis of this invention consist fundamentally in dividing the cell isolation process in three independent cell recovery phases and optimizing several technical parameters along the protocol. Such parameters were thus far either not mentioned or undefined in the state-of-the-art.

The tri-phased recovery method is based on the sequential recovery of the dissociated cells from three different independent origins along the isolation process: Phase 1—recovery of a first set of cells that are able to adhere to the surface of the cell culture flask where the tissue digestion reaction is performed. Adhesion occurs right after the digestion incubation period is over, with the flask being kept standing still in the horizontal position, for a period of 30 minutes, at room temperature, and still in the presence of the digestion solution. The adherent cells are then incubated in culture conditions and undergo expansion and multiplication until confluence reaches near 100%; Phase 2—recovery of a second set of cells from the supernatant which results from centrifugation of the digestion solution, after Phase 1. These cells are then incubated in culture conditions and the ones capable of adhering to the surface of a cell culture flask undergo expansion and multiplication until confluence reaches near 100%; Phase 3—recovery of a third set of cells from the pellet resulting from the centrifugation in Phase 2. These cells may be cryopreserved directly without adhesion, expansion, and multiplication.

Concerning the technical parameters optimized along the protocol, these are: 1—type of mechanical manipulation and initial umbilical cord fraction dimension, 2—presence or absence of blood clots within the umbilical vessels, 3—type of enzyme(s), individual or combined action and enzyme concentration(s) in the digestion solution, 4—composition of the digestion solution, 5—pH evolution during digestion reaction, 6—incubation period/time, 7—type of agitation (moderate or vigorous), 8—type of incubation atmosphere (dry or wet), and 9—cell density during cryopreservation.

The combination of a tri-phased method for dissociated cell recovery with optimization of the above mentioned technical aspects has generated a method more consentaneous with use in cell therapy, based on cell administration. This is due to the method's robustness (100% efficacy) and to the high cell yields obtained within a relatively short period of time. Furthermore, the cryopreservation methodology was also optimized in order to maximize cell viability for future use.

With the newly-developed method it is possible to obtain, from 100% of the umbilical cord samples processed, fact which is unprecedented in the state-of-the-art, in nine days, after direct freezing of a cell fraction, and after two independent single phases of adhesion and expansion/multiplication ex vivo (end of P0) of the majority of the cells, yields of approximately $8.6(\pm 0.1) \times 10^5$ cells/gram of processed umbilical cord. Such efficiency represents the possibility of obtaining, from one umbilical cord (average length of 35 cm), a total of $3.0 \times 10^7$ cells. In turn, the characteristics of the cells allow to obtain, for example, in 35 days (end of P6), an average of $7.7 \times 10^{15}$ cells, using a constant inoculum of $5.0 \times 10^5$ cells/cm$^2$ throughout the 6 passages, from 100% of the umbilical cord fractions processed. In the end, such efficiency represents a reduction in about 30% of the time needed to obtain the same number of cells with similar protocols existent in the state-of-the-art. According to what was described earlier, in order to obtain numbers near $1.0 \times 10^{15}$ cells, using the same initial inoculum, a minimum of 80 days would be necessary (Harris et al., 2006; Can and Karahuseyinoglu, 2007).

Although being specifically developed to cell therapy, the new method is also suitable for the creation of cell banks, to be used in gene therapy protocols, to be the basis for pharmacological and cosmetic compositions, to generate cells for production of molecules or molecular compounds, for producing cell layers for cell culture supports, and for producing cell lines through genetic manipulation.

BACKGROUND OF THE INVENTION

A precursor cell (stem, germinal, undifferentiated, or primitive) is a type of cell with self-renewal capacity for a significant time period and, above all, with the capacity of either partial or terminal differentiation into other types of more specialized cells.

Despite the enormous differentiation potential of embryonic precursor cells, their utilization for research or/and therapy is controversial and has raised serious ethical and safety issues. Thus, research in this area has been focusing on the identification and evaluation of alternative non-embryonic stem cells, such as those obtained from bone marrow, periostium, trabecular bone, adipose tissue, sinovial region, skeletal muscle, deciduous and definitive teeth pulp, and olfactory mucosa (Barry and Murphy, 2004; Roisen et al., 2001). It has already been demonstrated that cells isolated from these tissues have the capacity of differentiation inter alia into chondrocytes, adipocytes, osteoblasts, myoblasts, cardiomyocytes, astrocytes and tenocytes, both in vitro and in vivo (Carvalhal et al., 2007; Majumdar et al., 1998 e Pittenger et al., 1999). Such precursor cells, isolated from non-embryonic sources, and capable of differentiating into non-haematopoietic specialized cells, derived from the three germ layers (endoderm, mesoderm, and ectoderm), are denominated mesenchymal stem cells.

The major limitations to the utilization of mesenchymal precursor cells arise during clinical practice, namely during cell harvesting. Collection of mesenchymal cells invariably involves invasive methodologies to the donor, such as surgical procedures that (like collection of stem cells from bone marrow, for example) might even involve general anaesthesia. Furthermore, because mesenchymal stem cells are rare, the final number of cells obtained is generally low.

As an alternative, the umbilical cord tissues have been described as possible sources for adult precursor cells (Romanov et al., 2003). The umbilical cord blood, for example, is known to be a rich source for precursor cells but mainly of haematopoietic nature (blood lineage). Since mesenchymal stem cells are present in umbilical cord blood in limited numbers, attempts to isolate these cells from this tissue have resulted in some frustration, and even the most successful attempts, using very high amounts of blood, have not surpassed the 60% success rate, relative to the total number of tissue samples processed. And in the end, doubts still persisted about the origin of the isolated cells; that is, would the origin of cells have really been blood, or other foetal tissue (Chul-Wan et al., 2003; Bieback et al., 2004).

Other reports describe isolation of mesenchymal stem cells from other umbilical cord constituent tissues, considerably richer in mesenchymal nature than umbilical blood. Some examples of these procedures are based on umbilical cord matrix, also known by Wharton's jelly (Purchio et al., 1998; Mitchell et al., 2003; Davies et al., 2004; Wang et al., 2006); umbilical cord vein (Romanov et al., 2003; Auger et al., 2005), arterial tissues (Kadner et al., 2004); or other lining tissues, such as the amniotic membrane (Phan et al., 2004).

A detailed analysis reveals that the protocols described are, in one way or the other, restrictive in terms of the nature of the cells obtained, or rather vague in terms of success rate and efficiency in the number of cells isolated. In fact, the restrictive nature of these protocols invariably resulted in loss of phenotypic diversity of the cell populations isolated, mainly due to unnecessary focus on specific tissues or geographic locations within the umbilical cord structure. Furthermore, uncertainly invariably remained about the actual number of stem cells that could be obtained in the end.

Thus, for example, the Cell Research Corporation protocol that is based solely on the amniotic membrane as source of mesenchymal stem cells, originates cells already predisposed to the endothelial lineage (Phan et al., 2004).

Additionally, none of the methods described so far has demonstrated efficacy in terms of number of successful tissue samples processed in order to be reliable enough so as to be applied in cell therapy protocols. In other words, although the success rate for mesenchymal cell isolation from umbilical matrix is higher than from umbilical cord blood, or even bone marrow, there is no method up to now that guarantees 100% success rate for isolation, in terms of number of tissue samples processed, so that the final result is robust enough for cell therapy applications (Deryl e Weiss, 2008).

Furthermore, the introduction of unnecessary steps of structural manipulation, such as extraction of umbilical vessels (Purchio et al., 1998; Mitchell et al., 2003; Davies et al., 2004; Wang et al., 2006), or mechanical maceration (Seyda et al., 2006), makes existing protocols hard to standardize and reproduce, never assuring enough cell numbers for cell therapy application.

Furthermore, excessive tissue manipulation induces cell differentiation which is undesirable if one wants to maintain precursor cell phenotype (Gardner et al., 2000; Claes et al., 2002; Cullinane et al., 2003).

Also showing limitations are the protocols based on the umbilical vessels themselves. These protocols involve complex extractions of the arteries or the umbilical vein and limit the differentiation potential of mesenchymal stem cells to the sub-endothelial and endothelial lineages (Romanov et al., 2003; Auger et al., 2005; Kadner et al., 2004; Sarugaser et al., 2005).

Finally, no less complex, are the protocols that base themselves on the Wharton's jelly (WJ) as source for mesenchymal stem cells. These reports are not consistent, also contributing to the lack of definition and criteria of the applied methodologies. Thus, while Purchio et al., 1998; Mitchell et al., 2003; and Wang et al., 2006, perform a complex and hardly reproducible initial vessel extraction, processing the remaining tissue for cell isolation, Davies et al., 2004, also remove the umbilical vessels but, instead of using the remaining tissue, they process the tissue still coupled around the vessels for cell isolation, discarding the first. Nonetheless, all authors are unanimous in affirming that their protocols are based on WJ exclusively (Purchio et al., 1998; Mitchell et al., 2003; Davies et al., 2004; Wang et al., 2006). The discrepancy between these approaches is unjustified and the excess tissue manipulation of the existing tissues in either of these two protocols undermines desirable effects on precursor phenotype maintenance, and consequently endangers the utilization of the isolated precursor cells in isolation and cryopreservation services for the population in general.

The state-of-the-art is clearly missing a method based on a simple, robust, and defined protocol, so that it can be reproduced with guarantees of efficacy and efficiency. Once mesenchymal stem cells become applicable in cell therapy, it is necessary to assure to the patient that the method used for cell isolation will provide both the necessary quality and quantity of the therapeutic agent. Given the lack of guarantees presented by the protocols so far described in the state-of-the-art, it is foreseen that the present invention will suppress the need for a method with the above characteristics.

GENERAL DESCRIPTION OF THE INVENTION

The present invention intends to add to the state-of-the-art a selection method for isolation of precursor cells from human umbilical cord, with a specified mesenchymal character, based on a selection strategy through specific digestion of collagen, the support material of the umbilical cord matrix (Wharton's jelly).

Cell liberation occurs without mechanical manipulation of the initial tissue, thus ensuring that original cell phenotype remains intact and cell viability maintained. By "mechanical manipulation", in the present invention, it is meant maceration and/or crushing of any tissues in the sub-amniotic, intervascular, and perivascular regions of the umbilical cord; and/or extraction of umbilical cord vessels; and/or any other mechanical effect which might interfere with the stability, and consequently the phenotype and viability, of cells present in the umbilical cord matrix (Wharton's Jelly).

In addition to the absence of mechanical manipulation, the introduction of three independent phases for dissociated cell recovery and the optimization of several technical parameters along the process make the method simple, robust, 100% reliable in terms of efficacy, and highly efficient in terms of number of cells obtained related to time. As a result the method can be applied in cell therapy services, as well as cryopreservation of mesenchymal stem cells resulting from isolation for future autologous use.

The result of introducing a sequential three-phased process for cell isolation and the optimization of individual technical characteristics, thus far either not mentioned or described in an undefined fashion in the state-of-the-art, was evaluated according to the total cell yields obtained after each variable was introduced. Total cell yields correspond to a small cell portion which is frozen directly in the vapour phase of liquid nitrogen, without undergoing a phase of adhesion and expansion/multiplication plus two groups of cells previously isolated either from a first adhesion selection phase, right after tissue digestion, and a second adhesion selection phase, right after centrifugation of the digestion product. Both these sets undergo one phase of adhesion and expansion/multiplication and are cryopreserved once the corresponding cultures reach maximum confluence, before any passage (end of P0).

By "passage (P)", in the present invention, it is meant by the re-inoculum, preceded by trypsinization, of adherent cells, after the adherent cells have reached a confluence (cell density) at the growth surface of nearly 100%, due to their expansion/multiplication in a defined growth medium; so as to increase simultaneously the adhesion and expansion surface, as well as the total volume of growth medium, in order to initiate a new expansion/multiplication phase.

By "maximum confluence", in the present invention, it is meant by the growth surface of the culture support being uniformly covered by a single layer of cells.

The three sequential recovery phases comprising the tri-phased method are: Phase 1—recovery of a first set of cells that are able to adhere to the surface of the cell culture flask where the tissue digestion reaction is performed, still in the presence of the digestion solution. Phase 2—recovery of a second set of cells from the centrifugation of the digestion solution that are able to adhere to the surface of another cell culture flask in a solution consisting of supernatant and culture medium. Phase 3—recovery of a third set of cells from the pellet resulting from the centrifugation in Phase 2. These cells are cryopreserved directly without adhesion and expansion/multiplication.

In turn, the technical parameters optimized were:

1—Dimension of the initial tissue fractions to be used in the digestion reaction, maintaining a constant proportion of tissue mass (g), surface area of the bottom of the digestion flask ($cm^2$), digestion volume (ml), and the total volume of the flask (ml), of approximately 1:2:2:37, considering that a fraction of 1 cm of human umbilical cord weighs about 1 g. After removing the amniotic membrane, several types of fractionation methods were tested: low (5 cm fractions); medium (2.5 cm fractions); high (0.3 cm fractions); and minced tissue. All fractionations were performed with the help of a scalpel and the samples processed using exactly the same conditions. It was concluded that the best yields, in terms of total cells at the end of P0/umbilical cord mass/time, were obtained when using 2.5 cm fractions.

2—Presence or absence of blood clots within tissue vessels (1 vein and 2 arteries): it is known that lysis of red-blood cells is toxic, reducing cell viability in vitro. Therefore, cell yields were compared when the digestion was performed in the presence or absence of blood clots. For the latter, a scalpel was used to cause longitudinal incisions in the blood vessels in order to cause an aperture from which the clots could be removed. It was concluded that blood clots had a negative effect upon total cell yields.

3—Nature of the enzyme(s), concentration, and individual or combined action of the enzymes used in the tissue digestion step: direct cell adhesion to the culture flask, in the presence of culture medium, with no digestion, and therefore in the absence of enzymes; and tissue dissociation with a single enzyme: 0.075% (w/v) collagenase II or 2.0% (w/v) pronase were tested. Since the utilization of collagenase II alone was the most efficient approach, this enzyme was then combined with other enzymes, specifically with Trypsin 0.125% (w/v) (in the presence or absence of EDTA 0.260 mM), with hyaluronidase 0.5% (w/v) alone, and with hyaluronidase 0.5% (w/v) combined with pronase 2.0% (w/v). The best yields, in terms of total cells at the end of P0/umbilical cord mass/time, were obtained by the combined action of collagenase II 0.075% (w/v) with trypsin 0.125% (w/v). In addition, when the concentration of collagenase II was changed (0.0375%, 0.075% and 0.15% w/v), maintaining a trypsin concentration of 0.125% (w/v), in the presence of 0.260 mM EDTA, it was confirmed that the concentration of collagenase II of 0.075% (w/v) provided the best results, maintaining the previously optimized conditions constant.

4—Composition of the digestion solution: several enzymatic digestion solution compositions were tested, namely Alpha-Mem supplemented with 20% FBS and 1% Penicillin/streptomycin; saline buffer solution e.g. HBSS, supplemented with EDTA, more specifically with 186 mg/ml $CaCl_2.2H_2O$, 400 mg/ml KCl, 60 mg/ml $KH_2PO_4$, 200 mg/ml $MgSO_4.7H_2O$, 8000 mg/ml NaCl, 350 mg/ml $NaHCO_3$, 90 mg/ml $NaH_2PO4.7H_2O$, 1000 mg/ml glucose, and 76 mg/ml (0.260 mM) EDTA; the previous HBSS solution supplemented with 5 mM $CaCl_2$; 25 mM HEPES buffer supplemented with 5 mM $CaCl_2$. The saline buffer solution (HBSS), supplemented with 0.260 mM EDTA, produced the best yields.

5—Monitoring pH evolution during the digestion reaction: the pH was monitored along the digestion process and an acidification of the medium was noticed. In average, when using the combined action of collagenase II 0.075% (w/v), with trypsin 0.125% (w/v), in a Hank's salt solution (HBSS), supplemented with 0.260 mM EDTA, the initial pH was of 7.2, decreasing to 6.4 after 4 h incubation and to 5.9 after 16 h. The medium acidification can explain the lack of efficiency in cell isolation after long incubation periods (16 h). Despite the fact there are more complete digestions after long incubation periods the medium acidification becomes prejudicial for cell viability. The solution pH is therefore a parameter to take into consideration when planning incubation periods and should never be below 6.4 where it becomes prejudicial to the method's efficiency, as determined by counting viable isolated cells. Although more complete digestions were observed at 16 h, it was found that more extended periods had a negative impact on cell viability and led to a significant medium acidification 6—The incubation period/time for the digestion reaction: several incubation periods were tested (2 h, 4 h, 6 h, and 16 h). It was concluded that 4 h incubation produced the best yields.

7—Type of agitation (moderate or vigorous) during the incubation period of the digestion reaction: the incubation was performed in a water bath with orbital shaking with either moderate or vigorous oscillation rates, consisting of 100 oscillations per minute (opm) and 140 oscillations per minute (opm), respectively. The moderate agitation of 100 opm led to better results in terms of cell yields.

8—The atmosphere of incubation of the enzymatic digestion (dry or wet): the incubation was performed at 37° C. in two different environments: wet and dry. For this test tissue samples were processed in parallel either in an immersed orbital shaker, where the heat exchange occurred through both water and saturated air, or in a dry chamber, where heat exchange occurred through dry air. The incubation in the dry chamber resulted in better cell yields.

9—The effect of cell density in the cryopreservation efficiency of cells after undergoing one phase of adhesion and expansion/multiplication: 1 ml of cell suspensions was frozen at the end of P0 in the vapour phase of liquid nitrogen, at different densities (cells/ml), in a solution composed of 10% dimethyl sulfoxide (DMSO) and 90% foetal bovine serum (FBS). Cell viability after thaw (viable cells/total cells) and cell recovery (viable cells counted after thaw/viable cells counted before cryopreservation) were determined for each condition. The results obtained showed that a cell density of $3\times10^6$ cells/ml was the most likely to ensure a proper maintenance and recovery of viable cells after cryopreservation under the tested conditions.

In general, and given the optimizations described above, the invention is based on a selection method for isolating precursor cells from the human umbilical cord, where each umbilical cord is depleted of blood and transported to the laboratory in saline buffer, containing glucose and antibiotics, always in a sterile environment, preferably at room temperature if processed within 48 h. For longer storage periods, a temperature between 2° C. and 8° C. is advisable.

The following steps, involving processing the umbilical cord and isolating precursor cells, are performed in a vertical flux laminar flow hood chamber, under sterile conditions.

First, the amniotic membrane, which is the lining structure which has been in contact with the air during tissue collection, and thus more susceptible to microbial contamination, is peeled off and the umbilical cord is washed with a new salt solution.

Generically, in order to isolate the desired precursor cells, the method starts with fractions of defined dimension, derived from an optimized tissue fractioning which does not involve mechanical manipulation of the tissues, including any extraction of internal structures of the organ, except for blood clots within umbilical vessels when applicable.

The liberation of cells from the umbilical tissue is promoted by an enzymatic digestion directed towards the umbilical cord matrix, respecting an established proportional relationship between tissue mass (g), the surface of the digestion flask where the tissue is confined (cm²), the volume of digestion solution (ml), and the total volume of the digestion flask (ml), of approximately 1:2:2:37; considering that, in average, 1 cm fraction of umbilical cord weighs 1 g.

In order to proceed with the enzymatic digestion, a specific combination of enzymes is used, at specified concentrations, in a solution with defined composition, during an incubation period, at a specific minimum pH, and type of agitation and incubation atmosphere equally specified.

The recovery of dissociated cells proceeds in three phases where in a first phase a set of cells are recovered that are able to adhere to the surface of the cell culture flask where the tissue digestion reaction is performed. Adhesion occurs right after the digestion incubation period is over, with flask being kept standing still in the horizontal position, for a period between 10 and 120 minutes, preferably 30 minutes, at room temperature. In a second phase a new set of cells are recovered from the supernatant that results from centrifugation of the digestion solution, after Phase 1. In both, phase 1 and 2, cells are incubated in culture conditions and the ones capable of adhering to the surface of a cell culture flask undergo one phase of expansion/multiplication until confluence reaches near 100%. Finally, in Phase 3, a set of cells is recovered from the pellet resulting from the centrifugation in Phase 2 and cryopreserved directly without undergoing any round of adhesion and expansion/multiplication.

Sequential cell recovery and all the other optimized factors described previously were optimized so that the method presents 100% efficacy and maximum efficiency in terms of number of cells selected and isolated. In turn, the cell population obtained can be identified by the cells being capable of adhering and expanding/multiplying in a surface and defined growth medium, where the majority of cells in culture express the cell surface markers CD44, CD73, CD90 and CD105, and the majority of cells present only residual expression of the cell surface markers CD14, CD31, CD34 and CD45, where the majority of cells are able to undergo up to 18 expansion/multiplication phases, maintaining a constant duplication factor of approximately 1.7/24 h, a constant fibroblast-like morphology, and the capacity of partial or terminal differentiation into specialized cells, such as osteoblasts, chondrocytes, adipocytes, cardiomyocytes, and glial cells.

Additionally, the present invention contemplates the optimization of cell density (cells/vol) for cryopreservation of cells which undergo a round of adhesion and expansion/multiplication, with the aim of maximizing efficiency in terms of cell viability for future use.

With the new method it is possible to obtain, with every umbilical cord sample, a fact without precedents in the state-of-the-art, in nine days, after direct freezing of a cell fraction, and after two independent phases of adhesion and expansion/multiplication ex vivo (end of P0), yields of about $8.6(\pm0.1)\times10^5$ cells/gram of umbilical cord. Such efficiency represents the possibility of obtaining, from one umbilical cord (average length after collection 35 cm, approximately 35 g), a total of $3.0\times10^7$ cells. In turn, and since mesenchymal stem cells isolated typically present a duplication factor of 1.7/24 h, using a constant inoculum of $5.0\times10^5$ cells/cm², during 7 rounds (6 passages, P6) of adhesion and expansion/multiplication, in a cell culture flask with 175 cm² growth surface, it is possible to obtain, in 35 days, an average of $7.7\times10^{15}$ cells. This represents a 30% gain in the time needed to reach the same cell numbers using similar protocols described in the state-of-the-art, where in order to reach the same number of cells, with the same constant initial inoculum of $5.0\times10^5$ cells/cm², 80 days would be required (Harris et al., 2006; Can and Karahuseyinoglu, 2007).

Although the new method has been developed to be mainly applied in cell therapy protocols, it is also suitable for other ends, such as cell banking, gene therapy protocols, pharmacological and cosmetic compositions, production of molecules or molecular compounds, production of cell layers for cell culturing support, and for production of cell lines through genetic manipulation.

DETAILED DESCRIPTION OF THE INVENTION

Figure 1:
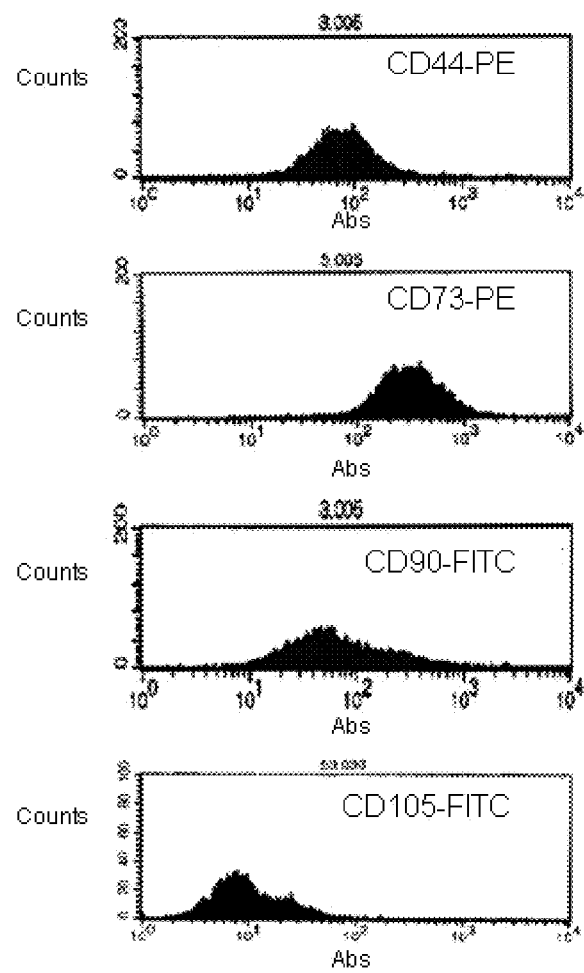
FIG. 1: Flow cytometry results with umbilical cord matrix-derived cells. Cells were immunolabelled using antibodies linked to PE or FITC against CD44 (97% positive cells), CD73 (99% positive cells), CD90 (97% positive cells) and CD105 (95% positive cells), all positive markers for mesenchymal stroma cells.

Prior to the application of the method the human umbilical cord should be separated from blood and transported to the laboratory facilities, in a sterile closed recipient, either dry, or preferably immersed in a sterile solution containing 186 μg/ml $CaCl_2.2H_2O$, 400 μg/ml KCl, 60 μg/ml $KH_2PO_4$, 200 μg/ml $MgSO_4.7H_2O$, 8000 μg/ml NaCl, 350 μg/ml $NaHCO_3$, 90 μg/ml $NaH_2PO4.7H_2O$, 2000 μg/ml glucose, and 1% of an equimolar mixture of penicillin and streptomycin, preferably at room temperature if processed within a period of 72 h, or between 2 and 8° C., preferably at 4° C., if processed within a period between 48 and 144 h after collection, without or preferably with a sterile saline solution, such as HBSS. The saline solution may be supplemented with nutrients and antibiotics, for example, 1 g/L glucose, 100 U/ml penicillin and 100 μg/ml streptomycin.

The method should be performed in a sterile environment, e.g., inside a laminar flow hood. The umbilical cord is washed 3 times with Hank's saline buffer solution (HBSS) and the amniotic membrane surrounding the umbilical cord is removed with the aid of sterile tweezers.

The umbilical cord is then transversally fractionated with the aid of a scalpel into approximately 2.5 cm fractions. Taking into account the average density of human umbilical cord (close to 1 g/cm), each fraction corresponds to approximately 2.5 g of tissue.

If present in these fractions, blood clots should be removed with the help of a scalpel. In the following steps, each group of seven 2.5 g blood clot-free fractions is treated independently.

Cells are obtained from the dissociation of each group of 7 fractions, performed in a sterile and sealed flask containing a digestion solution with buffered pH, by the combined action of collagenase II, at a concentration of 0.075% (weight/total digestion volume), with trypsin, at a concentration of 0.125% (weight/total digestion volume), maintaining a constant ratio between tissue mass, bottom surface area of the flask, digestion volume, and the total flask volume, of approximately 1:2:2:37, and where the flask is incubated under defined conditions of incubation time, temperature, heating environment, ambient humidity and agitation; more specifically, starting from a group of 7 umbilical cord fractions with approximately 2.5 cm (2.5 g) each, free from blood clots; using a volume of digestion solution of 35 ml; in a non-vented and closed culture flask, such as a $T_{175}$ with a total volume of 650 ml, and headspace during digestion of 615 ml minus the submerged volume of the 7 fractions under digestion; and where the digestion solution consists of, excluding the enzymes, 186 μg/ml $CaCl_2.2H_2O$, 400 μg/ml KCl, 60 μg/ml $KH_2PO_4$, 200 μg/ml $MgSO_4.7H_2O$, 8000 μg/ml NaCl, 350 μg/ml $NaHCO_3$, 90 μg/ml $NaH_2PO4.7H_2O$, 1000 μg/ml glucose, and 76 μg/ml (0.260 mM) EDTA; maintaining the pH at 6.4 or higher; and where the enzymatic reaction is incubated for 4 h; at a constant temperature of 37° C.; in a closed dry incubator; under agitation, at a constant rate of 100 oscillations·$min^{-1}$ (opm).

The recovery of cells obtained from tissue dissociation is performed in three phases (tri-phased method).

In a first phase, cells are recovered from the dissociated tissue, more specifically from a static horizontal incubation of the flask where the digestion took place for a time period of 5 to 300 minutes, preferentially of 30 minutes, at room temperature. The digestion supernatant is transferred by means of pipetting, avoiding suction of any undigested tissue, to a 50 ml centrifuge tube. Any undigested tissue is discarded. At this point, 35 ml of basal culture medium, supplemented with deoxyribonucleosides, ribonucleosides, glutamine, antibiotics and 10% of Foetal Bovine Serum (FBS) are added to the digestion flask. The non-vented flask cap is replaced by a filter containing vented cap and the digestion flask is incubated at 37° C. in a humidified atmosphere containing 7% $CO_2$. Changes of the total culture medium at every 72 h should be performed to promote the growth of cells that adhere during the horizontal incubation period (selection period), until maximum surface confluence is achieved.

In a second recovery phase, cells are recovered from a centrifugation of the digestion supernatant in a 50 ml centrifuge tube, at 350 g for 10 minutes, at room temperature. After centrifugation 35 ml of supernatant are transferred to a static culture flask ($T_{175}$) with a filter-containing vented cap; and 35 ml of basal culture medium supplemented with deoxyribonucleosides, ribonucleosides, glutamine, antibiotics and 10% of Foetal Bovine Serum (FBS) are added. The flask is then incubated at 37° C. in a humidified atmosphere containing 7% $CO_2$, and the total culture medium changed every 72 h in order to promote cell adhesion and expansion/multiplication until maximum surface confluence is achieved.

Cell populations obtained from the first and second phases are cryopreserved after the first adhesion and expansion/multiplication round (end of P0). This consists on the direct cryopreservation in the vapour phase of liquid nitrogen of a mixture of 0.5 ml of cell suspension, containing the desired total cell number, and the same volume of a solution of Foetal Bovine Serum (FBS) containing 10% of dimethyl sulfoxyde (DMSO), to obtain a final concentration of approximately $3 \times 10^6$ cells/ml, in a 1.5 ml sterile cryovial, containing therefore 1.0 ml cell suspension and 0.5 ml headspace.

The third and final phase of cell recovery consists on direct cryopreservation of the cell pellet obtained by the previously described centrifugation of the digestion supernatant, resuspended in 2 ml of a solution consisting of Foetal Bovine Serum (FBS), containing 10% of dimethyl sulfoxide (DMSO), using a controlled rate freezer, at a temperature decreasing rate of 1° C. $min^{-1}$, down to −80° C., in a 2.5 ml sterile cryovial, containing 2 ml cell suspension and 0.5 ml headspace.

Cryopreserved cells can be recovered whenever necessary through a fast thawing process in a water bath at 37° C. The cells are then resuspended in culture medium at the same temperature with a dilution factor of 1:10. Subsequent expansion rounds can be performed using inoculum densities between $5.0 \times 10^3$ and $2.0 \times 10^4$ cells/$cm^2$, with total medium exchange every 72 h. Cells typically exhibit a duplication factor of 1.7/24 h.

Example 1

Optimization of Type/Amount of Mechanical Manipulation and Fraction Dimension

The type of mechanical manipulation and size of initial tissue fragments were optimized maintaining a constant proportion of tissue mass (g), surface area of the bottom of the digestion flask ($cm^2$), digestion volume (ml), and the total volume of the flask (ml), of approximately 1:2:2:37, considering that a fraction of 1 cm of human umbilical cord weighs about 1 g. After removing the amniotic membrane, several types of umbilical cord fractionation were tested: low (5 cm fractions); medium (2.5 cm fractions); high (0.3 cm fractions); and minced tissue. All fractionations were performed with the help of a scalpel and the samples processed using exactly the same conditions. It was concluded that the best yields, in terms of total cells at the end of P0/umbilical cord mass/time, were obtained when using 2.5 cm fractions. Table 1 summarizes the results obtained qualitatively.

TABLE 1

Fractionation optimization: cell yield.

| Low (5 cm) | Medium (2.5 cm) | High (0.3 cm) | Mince |
|---|---|---|---|
| + | ++ | + | − |

Key:
+++ = Excellent,
++ = very good,
+ = good,
− = reasonable,
−− = bad,
0 = unsuccessful Example 2

Optimization Relative to the Presence or Absence of Blood Clots within Umbilical Cord Vessels (1 Vein and 2 Arteries)

It is known that lysis of red-blood cells is toxic, reducing cell viability in vitro. Therefore, cell yields were compared when the digestion was performed in the presence or absence of blood clots. For the latter experiment, blood clots were removed with the help of a scalpel. It was concluded that blood clots had a negative effect upon yield, in terms of total cells at the end of P0/umbilical cord mass/time. Table 2 summarizes the results obtained qualitatively.

TABLE 2

Blood clots: effects upon cell yield.

| Presence | Absence |
|---|---|
| − | ++ |

Key:
+++ = Excellent,
++ = very good,
+ = good,
− = reasonable,
−− = bad,
0 = unsuccessful Example 3

Optimization Relative to Enzyme Nature, Individual or Combined Enzyme Action, and Enzyme Concentration in the Digestion Solution In order to maximize yields, in terms of the number of cells with the desired characteristics isolated from the initial tissue, two initial approaches were adopted related to enzyme digestion: direct cell adhesion to the culture flask, in the presence of culture medium, with no digestion, and therefore in the absence of enzymes; and tissue dissociation with a single enzyme: 0.075% (w/v) collagenase II or 2.0% (w/v) pronase.

Since the utilization of collagenase II alone was the most efficient approach, this enzyme was then combined with other enzymes, specifically with Trypsin 0.125% (w/v) (in the presence or absence of EDTA 0.260 mM), with hyaluronidase 0.5% (w/v) alone, and with hyaluronidase 0.5% (w/v), combined with pronase 2.0% (w/v).

For these tests the optimal fraction size of 2.5 cm was used and the proportion of tissue mass (g), surface area of the bottom of the flask ($cm^2$), the volume of digestion (ml)

and the total volume of the flask (ml), of approximately 1:2:2:37 was maintained constant.

The results showed that the best yields, in terms of total cells at the end of P0/umbilical cord mass/time, were obtained by the combined action of collagenase II 0.075% (w/v) with trypsin 0.125% (w/v). In addition, when the concentration of collagenase II was changed (0.0375%, 0.075% and 0.15% w/v), maintaining a trypsin concentration of 0.125% (w/v), in the presence of 0.260 mM EDTA, it was confirmed that the concentration of collagenase II of 0.075% (w/v) provided the best result. Table 3 qualitatively summarizes these results.

TABLE 3

Enzyme nature, combined action and concentration: effects upon cell yield.

|  | No enzyme | Pronase (2.0%) | Col II (0.0375%) | Col II (0.075%) | Col II (0.150%) |
|---|---|---|---|---|---|
| No enzyme | ○ | -- | - | + | -- |
| Trypsin (0.125%) | X | X | + | + | -- |
| Trypsin (0.125%) + EDTA (0.260 mM) | X | X | X | ++ | X |
| Hyaluronidase (0.5%) | X | X | X | + | X |
| Pronase (2.0%) + Hyaluronidase (0.5%) | X | X | X | + | X |

Key:
+++ = Excellent,
++ = very good,
+ = good,
- = reasonable,
-- = bad,
○ = unsuccessful Example 4

Optimization of the Chemical Composition of the Enzymatic Solution

Several enzymatic digestion solution compositions were tested, namely, Alpha-Mem supplemented with 20% FBS and 1% Penicillin/streptomycin; saline buffer solution e.g. HBSS, supplemented with EDTA, more specifically with 186 mg/ml $CaCl_2.2H_2O$, 400 mg/ml KCl, 60 mg/ml $KH_2PO_4$, 200 mg/ml $MgSO_4.7H_2O$, 8000 mg/ml NaCl, 350 mg/ml $NaHCO_3$, 90 mg/ml $NaH_2PO4.7H_2O$, 1000 mg/ml glucose, and 76 mg/ml (0.260 mM) EDTA; the previous HBSS solution supplemented with 5 mM $CaCl_2$; 25 mM HEPES buffer supplemented with 5 mM $CaCl_2$.

For these tests the previously optimized conditions were maintained, namely the enzyme combination consisting of collagenase II 0.075% (w/v) and trypsin 0.125% (w/v).

The best results were obtained for the saline buffer solution (HBSS), supplemented with 0.260 mM EDTA. Table 4 qualitatively summarizes the results obtained.

TABLE 4

Composition of the enzymatic solution: effects upon cell yield.

|  | Alpha-Mem + 20% FBS + 1% pen/strep | HBSS + 0.26 mM EDTA | HBSS + 5 mM $CaCl_2$ | 25 mM HEPES + 5 mM $CaCl_2$ |
|---|---|---|---|---|
| Col II (0.075%) + Trypsin (0.125%) | -- | ++ | - | + |

Key:
+++ = Excellent,
++ = very good,
+ = good,
- = reasonable,
-- = bad,
0 = unsuccessful Example 5

Optimization of Enzymatic Digestion Incubation Time and pH Evolution

Several incubation periods were tested: 2 h, 4 h, 6 h and 16 h. From the results obtained the best incubation period was 4 h. Although more complete digestions were observed at 16 h, it was found that more extended periods had a negative impact on cell viability and led to a significant medium acidification. Table 5 qualitatively summarizes the results obtained.

TABLE 5

Incubation time and pH of enzymatic digestion solution: effects upon cell yield.

|  | 2 h | 4 h | 6 h | 16 h |
|---|---|---|---|---|
| Col II (0.075%) + Trypsin (0.125%) in HBSS + 0.26 mM EDTA | + (pH 6.9) | ++ (pH 6.4) | - (pH 6.1) | + (pH 5.9) |

Key:
+++ = Excellent,
++ = very good,
+ = good,
- = reasonable,
-- = bad,
0 = unsuccessful Example 5

Optimization of Agitation Mode (Moderate Versus Vigorous) During Digestion

The incubation of the enzymatic digestion solution was performed in a water bath with orbital shaking with either moderate (100 opm) or vigorous (140 opm) oscillation rates. The moderate agitation of 100 opm led to better results in terms of cell yield. Table 6 qualitatively summarizes the results obtained.

TABLE 6

Agitation rate: effects upon cell yield.

| 100 opm | 140 opm |
|---|---|
| ++ | + |

Key:
+++ = Excellent,
++ = very good,
+ = good,
− = reasonable,
−− = bad,
0 = unsuccessful Example 7

Optimization of the Incubation Atmosphere During Enzymatic Digestion (Dry Versus Wet)

The incubation of the enzymatic digestion solution was performed at 37° C. in two different environments: wet and dry. For this test tissue samples were processed in parallel either in an immersed orbital shaker, where the heat exchange occurred through both water and saturated air, or in a dry chamber, where heat exchange occurred through dry air. The incubation in the dry chamber resulted in better cell yields. Table 7 summarizes the results obtained qualitatively.

TABLE 7

Incubation environment: effects upon cell yield.

| Water bath | Dry chamber |
|---|---|
| ++ | +++ |

Key:
+++ = Excellent,
++ = very good,
+ = good,
− = reasonable,
−− = bad,
0 = unsuccessful Example 8

Optimization of Cell Density During Cryopreservation

To evaluate the effect of cell density upon cell recovery after cryopreservation, cells were frozen at the end of P1 in the vapour phase of liquid nitrogen, at different densities ranging between $1 \times 10^6$ and $10 \times 10^6$ cells/ml, in 1.5 ml cryotubes containing 0.5 ml of cell suspension and the same volume of a solution composed of FBS (90%) and DMSO (10%).

Cells were cryopreserved for a minimum of 30 days and then thawed by placing the cryotube in a water bath kept at 37° C. Thawed cells were resuspended in 10 ml of culture medium previously heated to 37° C. Total and viable cells were counted and subsequently inoculated in tissue culture flasks (NUNC) at a dilution factor of 1:10.

After 24 h the medium was exchanged for fresh medium and cells were maintained as described above.

To determine the optimal cell density for cryopreservation, cell viability after thaw (viable cells/total cells) and cell recovery (viable cells counted after thaw/viable cells counted before cryopreservation) were determined for each condition. The results obtained showed that a cell density of $3 \times 10^6$ cells/ml was the most likely to ensure a proper maintenance and recovery of viable cells after cryopreservation under the tested conditions (1.5 ml cryotubes containing 1 ml of cell suspension and 0.5 ml headspace).

Figure 4:
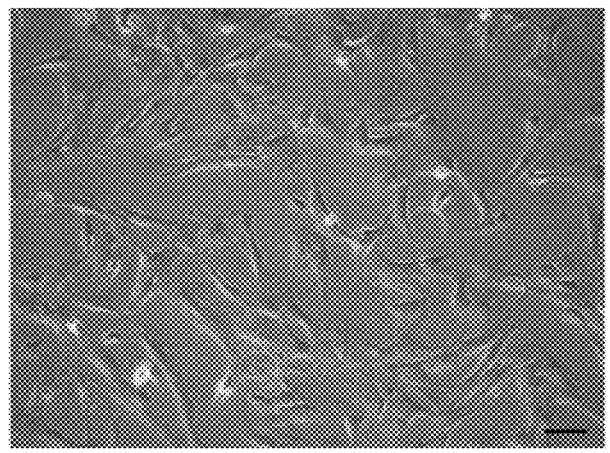
FIG. 4: In vitro expansion of thawed cells. The duplication factor observed was 1.7/24 h, similar to that observed for these cells prior to cryopreservation. A confluence of 80-90% was observed 36 h after thawing (with medium exchange after 24 h): A—Precursor cells 12 h after thawing, before medium exchange. B—Precursor cells 36 h after thawing (medium exchange performed after 24 h). Bar: 100 m.
Figure 4:
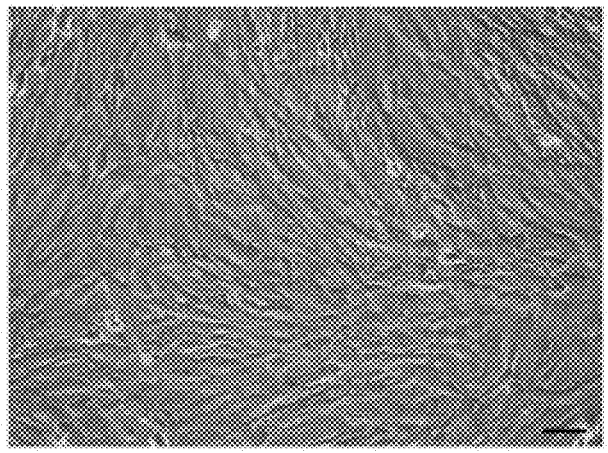

The in vitro expansion capacity of the thawed cells was monitored. Cells typically exhibited a duplication factor of 1.7 doublings per day, similar to the value observed before cryopreservation (FIG. 4).

Example 9

Isolation of Precursor Cells from Human Umbilical Cords Using the Method Developed After obtaining authorization from the Ethics Committees of the institutions where the umbilical cords were collected and informed consent from the mothers, several umbilical cords were collected after giving birth. The umbilical cords were separated from the placenta, depleted of blood and transported to the laboratory facilities in a sterile closed flask containing a sterile saline solution, HBSS, supplemented with nutrients and antibiotics, for example, 1 g/L glucose, 100 U/ml penicillin and 100 µg/ml streptomycin.

The transport to the facilities was performed at room temperature. The method was performed in a sterile environment inside a laminar flow hood.

Each umbilical cord was washed 3 times with Hank's saline buffer solution (HBSS) and the amniotic membrane surrounding the umbilical cord was removed with sterile tweezers.

Each umbilical cord was then transversally fractionated with the help of a scalpel into 2.5 cm fractions. Taking into account the average linear density of human umbilical cord (1 g/cm), each fraction corresponds to approximately 2.5 g of tissue. In these fractions, identified blood clots were removed with the help of a scalpel. Each group of seven 2.5 g blood clot-free fractions was treated independently.

Cells were obtained from the dissociation of each group of 7 fractions, performed in a sterile and sealed flask containing a digestion solution with buffered pH, by the combined action of collagenase II, at a concentration of 0.075% (weight/total volume of digestion), with trypsin, at a concentration of 0.125% (weight/total volume of digestion), maintaining a constant ratio between tissue mass, surface area of the bottom of the flask, the volume of digestion and the total volume of the flask, of approximately 1:2:2:37. The flask was incubated under defined time period, temperature, heating environment, ambient humidity and agitation; more specifically, starting from a group of 7 umbilical cord fractions with approximately 2.5 g each, free from blood clots, using a volume of digestion solution of 35 ml, in a non-vented closed culture flask, like a T175 of a total volume of 650 ml and a headspace during digestion of 615 ml minus the submerged volume of the 7 fractions under digestion and where the digestion solution consists, excluding the enzymes, of 186 mg/ml $CaCl_2 \cdot 2H_2O$, 400 mg/ml KCl, 60 mg/ml $KH_2PO_4$, 200 mg/ml $MgSO_4 \cdot 7H_2O$, 8000 mg/ml NaCl, 350 mg/ml $NaHCO_3$, 90 mg/ml $NaH_2PO4 \cdot 7H_2O$, 1000 mg/ml glucose, and 76 mg/ml (0.260 mM) EDTA, maintaining the pH at 6.4 or higher. The enzymatic reaction was incubated for 4 h, at a constant temperature of 37° C. in a closed dry incubator, under agitation at a constant rate of 100 oscillations·min$^{-1}$ (opm).

The recovery of the cells obtained from tissue dissociation was performed in three phases.

In a first phase, cells were recovered from the dissociated tissue, more specifically from a static horizontal incubation of the flask where the digestion took place for a time period of 5 to 300 minutes, preferentially of 30 minutes, at room temperature. The digestion supernatant was transferred by means of pipetting, avoiding any undigested tissue, to a 50 ml centrifuge tube. All the undigested tissue was discarded. At this point, 35 ml of basal culture medium supplemented with deoxyribonucleosides, ribonucleosides, glutamine, antibiotics and 10% of Foetal Bovine Serum (FBS) were added to the digestion flask. The non-vented flask cap was substituted by a filter containing vented cap and the digestion flask was incubated at 37° C. in a humidified atmosphere containing 7% $CO_2$. Changes of the total culture medium at every 72 h for 7 days were performed to promote the growth of cells that adhered during the horizontal incubation, until surface confluence with cells was achieved.

In a second recovery phase, cells are recovered from the centrifugation of the 50 ml centrifuge tube from above at 350 g, for 10 minutes, at room temperature and by transferring the 35 ml supernatant volume after centrifugation to a static culture flask, such as a $T_{175}$ with a filter-containing vented cap; adding to the same culture flask 35 ml of basal culture medium, supplemented with deoxyribonucleosides, ribonucleosides, glutamine, antibiotics and 10% of Foetal Bovine Serum (FBS); incubating the culture flask at 37° C., in a humidified atmosphere, containing 7% $CO_2$; and changing the culture medium every 72 h in order to promote adhesion and cell expansion/multiplication until maximum confluence is achieved.

The cell populations obtained from the first and second phases were cryopreserved at the end of the first expansion cycle (end of P0). This consisted on the direct cryopreservation in the vapour phase of liquid nitrogen of a mixture of 0.5 ml of cell suspension, containing the desired total cell number, and the same volume of a solution of Foetal Bovine Serum (FBS) containing 10% of dimethyl sulfoxyde (DMSO), to obtain a final concentration of approximately $3 \times 10^6$ cells/ml, in a 1.5 ml sterile cryovial containing 1.0 ml of cell suspension and 0.5 ml of headspace.

The third and final phase of cell recovery from the dissociated tissue consisted on the direct cryopreservation of the cell pellet obtained by centrifugation of the digestion supernatant, using a controlled rate freezer at a temperature decreasing rate of $1° C. \cdot min^{-1}$ down to −80° C., where cells were resuspended in 2 ml of a solution of Foetal Bovine Serum (FBS) containing 10% of dimethyl sulfoxyde (DMSO) in a 2.5 ml sterile cryovial containing 2 ml of cell suspension and 0.5 ml of headspace.

Cryopreserved cells were recovered after 31 days through a fast thawing process in a water bath at 37° C. The cells are then resuspended in culture medium at the same temperature with a dilution factor of 1:10. Subsequent expansion steps can be performed using inoculum densities between $5.0 \times 10^3$ and $2.0 \times 10^4$ cells/cm$^2$, with total medium exchange every 72 h. Cells typically exhibit a growth rate of 1.7 doublings per day for 18 passages.

Example 10

Certification of the Mesenchymal Phenotype of the Isolated Precursor Cells

Beyond the capability to adhere and proliferate in a selective culture medium for precursor mesenchymal cells, the isolated cells were characterized at the end of P1, by flow cytometry.

When the cells reached 80% to 90% confluence at the end of P1, the culture medium was removed and the cell surface washed with phosphate buffer (without $Ca^{2+}$ and $Mg^{2+}$). Trypsin at 0.25% was added and, as soon as cells detach from the flask surface, 2 volumes of culture medium were added. The cell suspension was then centrifuged for 10 minutes at 350 g, and the supernatant was discarded. The pellet containing the cells was resuspended in blocking solution (0.2% BSA in dPBS) to achieve a final cell concentration between $2 \times 10^6$ and $10 \times 10^6$ cells/ml. After an incubation period of 10 minutes at room temperature, 100 l of the cell suspension were added to each tube containing the primary antibodies conjugated with a fluorescence marker, Phycoerythrin (PE) or Fluorescein Isotiocyanate (FITC). The cell suspension was shaken and incubated in ice and protected from light for 20-40 min. After this period, 1.5 ml of dPBS were added to each tube, the cells were resuspended and centrifuged for 5 minutes at 350 g. The supernatant was discarded and the pellet containing the cells was resuspended in 500 l of paraformaldehyde at 1%.

Figure 2:
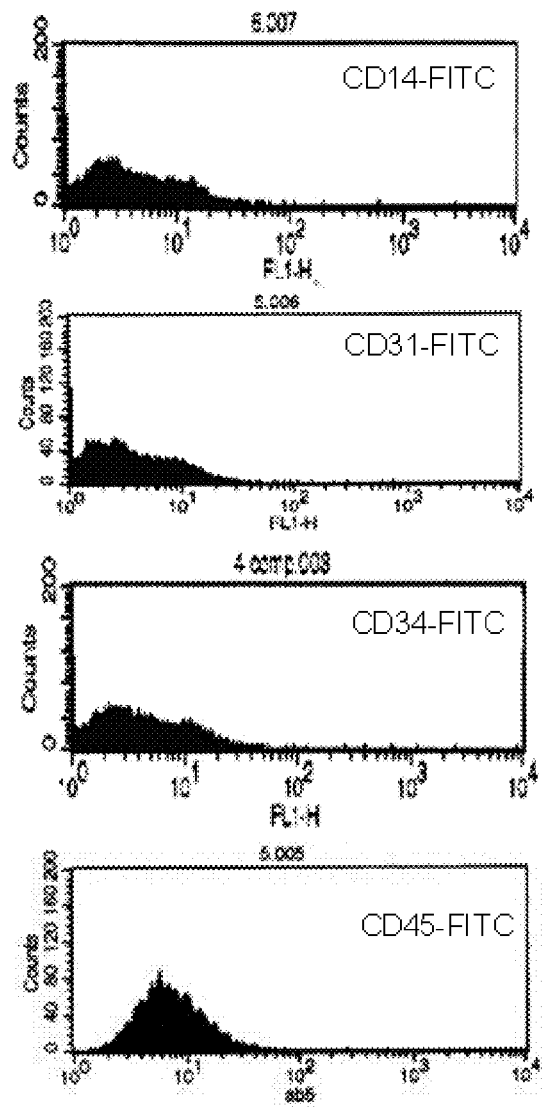
FIG. 2: Flow cytometry results with umbilical cord matrix-derived cells. Cells were immunolabelled using antibodies linked to PE or FITC against antigens known to be negative markers for the mesenchymal lineage: CD14, monocytic lineage (<1% positive cells), CD34, specific for haematopoietic lineage (1.2% positive cells), CD31, endothelial marker (1% positive cells), and CD45 (1.1% positive cells), panleukocyte marker.
Figure 3:
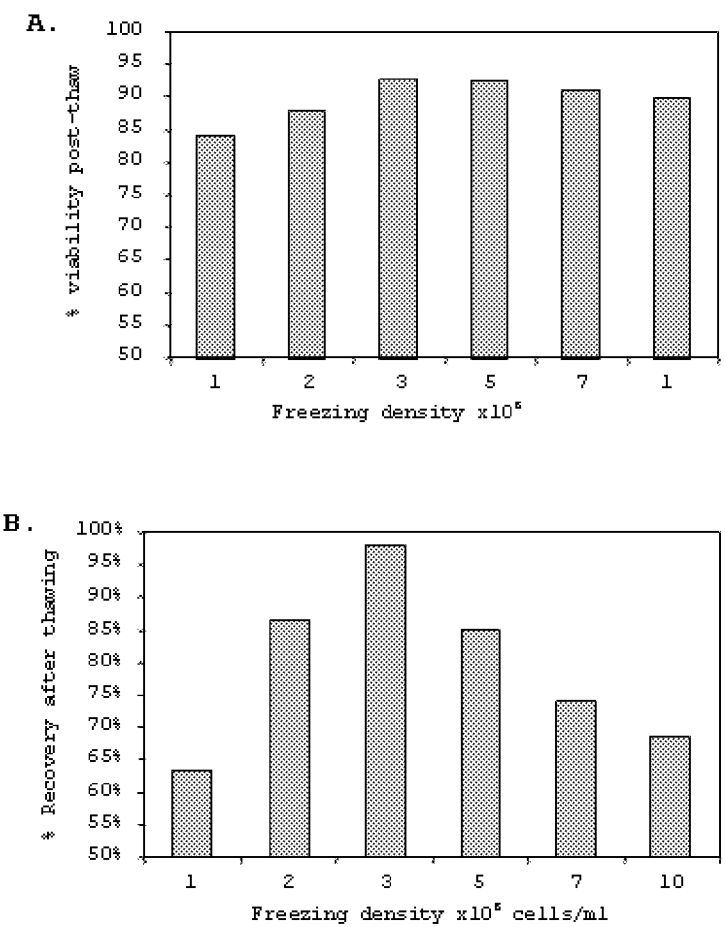
FIG. 3: Effect of cell density upon the efficiency of cell cryopreservation after cell adhesion and expansion/multiplication: A—post-thaw viability (viable cells/total cells× 100%) for different cell densities. B—Cell recovery (viable cells recovered after thawing/initial number of viable cells frozen). The best results were obtained with a cell density of $3×10^6$ cells/ml for the conditions tested (1.5 ml sterile cryotubes containing 1 ml of cell suspension and 0.5 ml of headspace).

The cell suspension was stored at 4° C. until further use. The flow cytometry was performed in a FACScalibur from BD Biosciences with the detection of CD44, CD73, CD90 and CD105 surface antigens as positive markers of mesenchymal cells. For this, primary antibodies conjugated to FITC or PE were used (FIG. 1). The presence of the negative markers CD14, CD31, CD34 and CD45 surface antigens was investigated. These are specific for the haematopoietic (CD34), monocytic (CD14), endothelial (CD31) and pan-leucocytic (CD45) lineages and all of these antibodies were conjugated to FITC (FIG. 2). As expected, the large majority of the isolated mesenchymal cells showed to be positive for CD44, CD73, CD90 and CD105 and negative or only residually positive for the above referred negative markers.

Example 11

Demonstration of the Precursor Phenotype of the Isolated Cells: Osteogenic Differentiation In accordance with the detailed description of the invention, the precursor cells isolated from the fractions of human umbilical cord, showed the capacity to differentiate into different specialized cell types. In this example the differentiation capabilities of these cells into osteoblasts is demonstrated.

Cells were inoculated at P3 at a density of $2.0 \times 10^4$ cells/cm$^2$ in osteogenic differentiation medium containing alpha-MEM basal medium (with deoxyribonucleotides, ribonucleotides and ultraglutamine) supplemented with 10% fetal bovine serum (FBS), 10 mM β-glycerophosphate, 100 U/ml penicillin, 100 µg/ml streptomycin, 50 µg/ml ascorbate-2-phosphate, 100 nM dexamethasone (Hung et al., 2002).

The entire medium was changed 2 times per week for 3 weeks after which the specific staining protocols, using alizarin red and alkaline phosphatase were performed and were both positive. Regarding the alizarin red staining, the medium was carefully aspirated from the tissue culture flask and cells were fixed with 4% para-formaldehyde for 10 minutes at room temperature.

Cells were washed with PBS and incubated with the specific staining solution, alizarin red S, 40 mM, pH4.2, for 15 minutes at room temperature. The alizarin red S solution was removed and the cells carefully washed with water (Kotobuki et al., 2006).

In the case of the alkaline phosphatase (Sigma-Aldrich) test, the cells were also fixed with 4% para-formaldehyde for 10 minutes at room temperature. The cells were then washed with PBS and submerged in 2.5 ml of citrate solution and left to incubate for 30 seconds.

Figure 5:
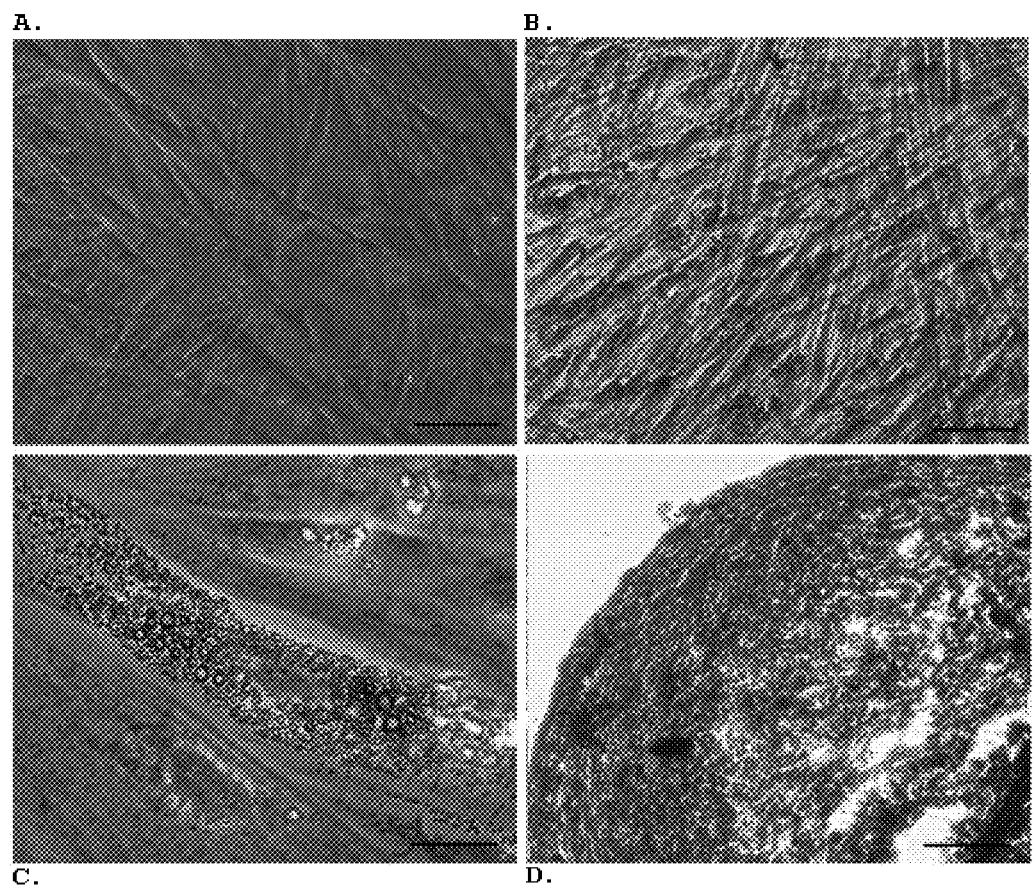
FIG. 5: Differentiation of isolated precursor cells into osteoblasts, adipocytes and chondrocytes. A—Cell morphology of control cells (non-differentiated cells) in normal growth medium. B—Osteogenic differentiation: cells were inoculated in osteogenic differentiation medium and maintained for 3 weeks before staining with alkaline phosphatase. C—Adipogenic differentiation: adipogenic differentiation medium was added to fully confluent cell cultures and cells were maintained for 3 weeks before staining with Oil-O-red. D—Chondrogenic differentiation: cells were resuspended and maintained in a centrifuge tube in chondrogenic differentiation medium for 4 weeks. Cells were then stained with Alcian blue and haematoxylin. Bar: 100 m.

The citrate solution was then removed and the cells washed with deionized water (milliQ) and incubated with the staining solution, Neutral red, for 2 minutes. The solution was then removed and the cells carefully washed with water (Shim, et al., 2004). The test was positive for osteogenic differentiation (FIG. 5).

Example 12

Demonstration of the Precursor Phenotype of the Isolated Cells: Adipogenic Differentiation In order to differentiate cells into adipocytes, the cells were plated at P3 at a density of $2.0 \times 10^4$ cells/cm$^2$ in alpha-MEM basal medium (with deoxyribonucleotides, ribonucleotides and ultraglutamine) supplemented with 10% FBS, 100 u/ml penicillin and 100 µg/ml streptomycin and maintained in this culture medium. When confluent, the medium was changed to adipogenic differentiation medium with consisted of DMEM-LG with 10% FBS, 100 U/ml penicillin, 100 µg/ml streptomycin, 10 µg/ml insulin, 200 M indometacin, 0.5 mM isobutyl-1-methylxanthine and 1 M dexamethasone (Shih et al., 2005).

The entire medium was changed 2 times per week during 3 weeks, after which the specific staining assays with Oil red O were performed and adipogenic differentiation confirmed. For this, the culture medium was carefully removed from the tissue culture flasks (NUNC) by aspiration and the cells fixed with 4% para-formaldehyde for 10 minutes at room temperature. The cells were then washed with PBS and incubated with the filtered Oil red O solution (2:3) for at least 10 minutes at room temperature. The Oil red O solution was then removed and the cells carefully washed with water (Do, et al., 2006). The test was positive for adipogenic differentiation (FIG. 5).

Example 13

Demonstration of the Precursor Phenotype of the Isolated Cells: Chondrogenic Differentiation For chondrogenic differentiation, cells were resuspended at P3 to a final density of $1.1 \times 10^6$ cells/ml and placed in a conical 15 ml tube in order to let the chondrospheres to form. The culture medium used was chondrogenic differentiation medium consisting on DMEM-LG with 1% FBS, 6.25 µg/ml insulin, 10 ng/ml TGFβ1 and 50 µM ascorbate-2-phosphate (Shih et al., 2005).

The entire medium was changed twice a week for 4 weeks with special care as not to disturb the chondrospheres, after which the specific staining assays with alcian blue and hematoxylin were performed and chondrogenic differentiation confirmed. For this, the entire medium was removed from the tube by aspiration and the chondrospheres washed with PBS. The chondrospheres were then submerged in agar and frozen in the liquid nitrogen vapor phase.

With the aid of a microtome, the agar was cut in 5 µm thick tissue sections. These sections were stained with 1% alcian blue and incubated for 5 minutes at room temperature and then washed with PBS. The preparations fixed on a microscope slide were passed through a hematoxylin solution and incubated for 5 minutes at room temperature. The hematoxylin was removed by a final washing step with PBS (Okada, et al., 2005). The test resulted positive for chondrogenic differentiation (FIG. 5).

Example 14

Demonstration of the Precursor Phenotype of the Isolated Cells: Cardiomyogenic Differentiation Cardiomyogenic differentiation occurred for a period of 18 days, during which different culture media were used (Lee et al., 2004). The cells were plated at a density of 3000 cells/cm$^2$ in a 16-well chamber slide coated with ornithine. Cells were plated in Medium C0 which consisted of Alpha-MEM basal medium (with deoxyribonucleotides, ribonucleotides and ultraglutamine) supplemented with 10% FBS, 100 U/ml penicillin and 100 µg/ml streptomycin. Twenty four hours after plating, the culture medium was replaced with another medium (Medium C1) which consisted of DMEM-LG supplemented with 10% FBS, 100 U/ml penicillin, 100 µg/ml streptomycin, 2 mM L-glutamine, 10 ng/ml β-FGF and 10 µM 5-azacytidine. Twenty four hours after plating the cells in Medium C1, a second medium change was performed to Medium C2. Medium C2 consisted of DMEM-LG basal medium supplemented with 10% FBS, 100 U/ml penicillin, 100 µg/ml streptomycin, 2 mM L-glutamine and 10 ng/ml β-FGF. Cells were maintained in Medium C2 for two weeks, with medium changes every 72 hours.

Figure 6:
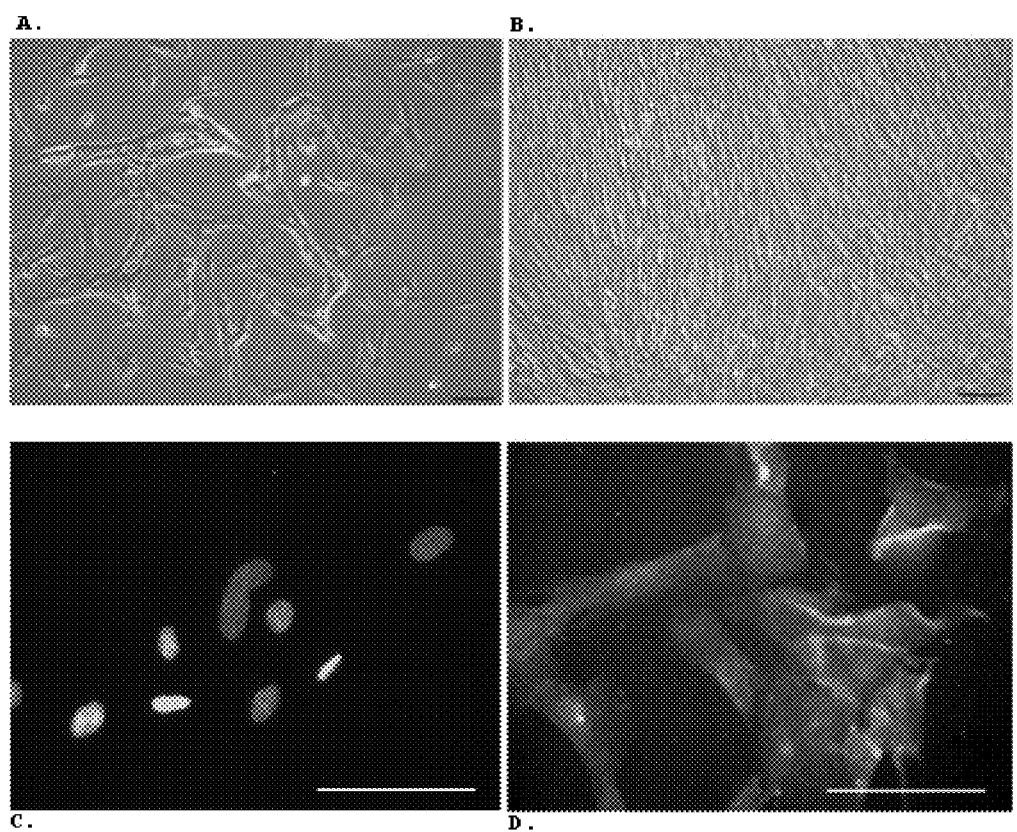
FIG. 6: Differentiation of precursor cells isolated into cardiomyocytes. A—Cell morphology of control cells (non differentiated cells) in normal growth medium, Alpha-Mem, supplemented with 10% FBS and 1% Penicillin/Streptomycin. B—Cell morphology after cardiomyogenic differentiation. C—Control cells (non-differentiated cells) marked with DAPI and with an antibody against Troponin T, a specific cardiomyocyte marker. Only DAPI marked nuclei are observed. D—Differentiated cells marked with DAPI and with an antibody against Troponin T. Both, DAPI marked nuclei and Troponin T marked cytoskeleton, can be observed.

In parallel, control (non-differentiated) cells were plated at a density of 5000 cells/cm$^2$ and maintained in Medium 0. After the differentiation period, immunofluorescence assays were performed with primary antibodies against a typical muscle protein, cardiac troponin T, specific to cardiomyocytes. In order to locate cells for the assay, the cellular nuclei were stained with a fluorochrome, DAPI, specific for nucleic acids. As it was expected, only cells subjected to the cardiomyogenic differentiation protocol, already presenting typical cardiomyocyte morphology, produced a fluorescent signal (FIG. 6D).

Example 15

Demonstration of the Precursor Phenotype of the Isolated Cells: Neurogenic/Glial Differentiation The neurogenic differentiation occurred for a period of 12 days, during which different culture media were used (Lee et al., 2004). The cells were plated at a density of 3000 cells/cm$^2$ in 16-well chamber slides coated with ornithine. Cells were plated in culture medium (Medium N1), consisting of basal IMDM medium supplemented with 10% FBS, 100 U/ml penicillin, 100 µg/ml streptomycin, 2 mM L-glutamine (Sigma), 5 ng/ml β-FGF, 0.5 µM retinoic acid and 1 mM 2-mercaptoethanol.

Three days after plating, Medium N1 was replaced with Medium N2 containing basal IMDM medium supplemented with 10% FBS, 100 U/ml penicillin, 100 µg/ml streptomycin, 2 mM L-glutamine, 1 mM cyclic adenosine monophosphate (cAMP) and 100 µM ascorbate-2-phosphate.

Three days after plating, Medium N2 was replaced with Medium N3 containing IMDM basal medium supplemented with 10% FBS 100 U/ml penicillin, 100 µg/ml streptomycin, 2 mM L-glutamine, 1 mM cyclic adenosine monophosphate (cAMP) and 10 µM hydrocortisone.

Finally, 3 days after plating, Medium N3 was replaced with Medium N4 consisting of IMDM basal medium supplemented with 10% FBS, 100 U/ml penicillin, 100 µg/ml streptomycin, 2 mM L-glutamine, 20 ng/ml FGF-1, 10 ng/ml SHH, 10 ng/ml NGF, 25 ng/ml vitronectin, 100 μM ascorbate-2-phosphate, 100 μM isobuthylmethylxantine, 10 μM forskolin and 20 nM PMA.

In parallel, control (non-differentiated) cells were plated at a density of 5000 cells/cm$^2$ and maintained in Medium N0 (see cardiomyogenic differentiation protocol).

Figure 7:
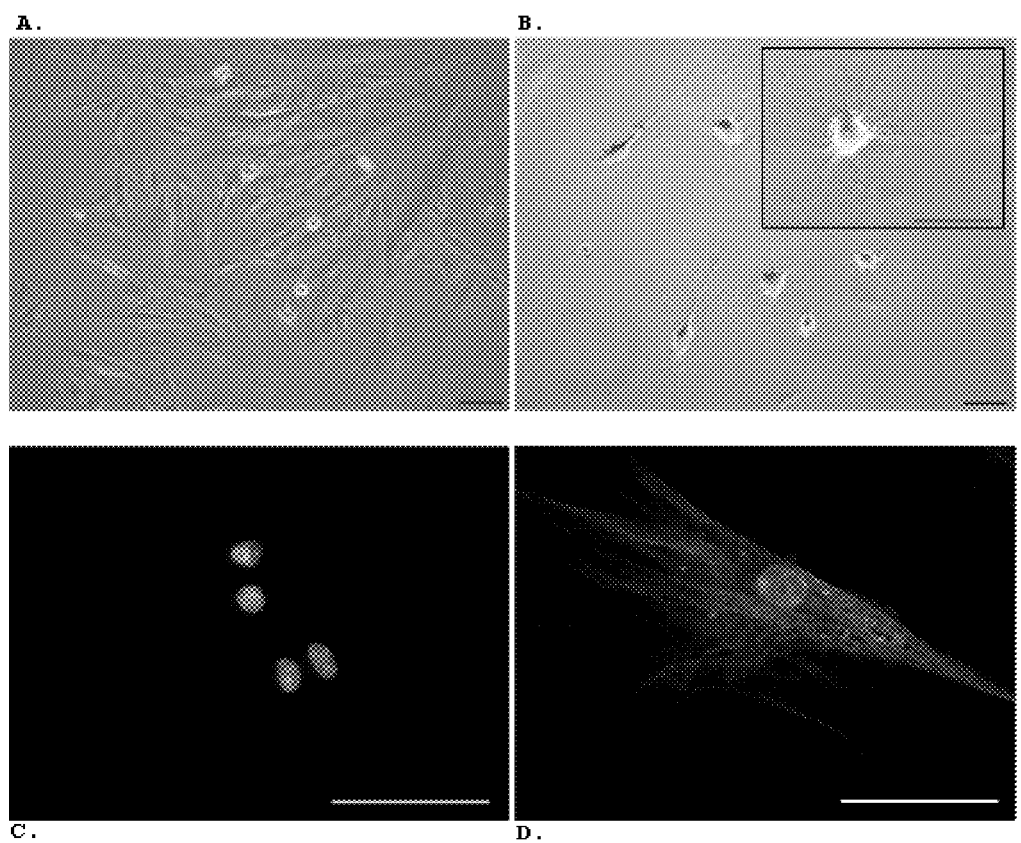
FIG. 7: Differentiation of precursor cells isolated into glial/neural cells. A—Cell morphology of control cells (non differentiated cells) in normal growth medium, Alpha-Mem, supplemented with 10% FBS and 1% Penicillin/Streptomycin. B—Cell morphology after glial/neural differentiation. C—Control cells (non-differentiated cells) marked with DAPI and with an antibody against—tubulin III, a specific neuronal protein. Only DAPI marked nuclei are observed. D—Differentiated cells marked with DAPI and with an antibody against—tubulin III. Both, DAPI marked nuclei and—tubulin III marked cytoskeleton, can be observed.

After the differentiation period, immunofluorescence assays were performed with a primary antibody against β-tubulin, type III, specific for neuronal cells. In order to locate the cells for the assay, the cellular nuclei were stained with a fluorochrome, DAPI, specific for nucleic acids. As was expected, only cells subjected to the neurogenic/glial differentiation protocol, already presenting a typical glial morphology (FIG. 7B), produced a fluorescent signal (FIG. 7D).

REFERENCES

Auger F. A., Germain L., Remy-Zolghadri M. and C. J. Hayward (2005). Method of isolating cells from umbilical cord. WO2005001081.

Barry F. P. and J. M. Murphy (2004) Mesenchymal stem cells: clinical applications and biological characterization. Int. J. Biochem. & Cell Biol. 36:568-584.

Can A. and S. Karahuseyinoglu (2007). Concise review: human umbilical cord stroma with regard to the source of fetus-derived stem cells. Stem Cells (on line—www-.StemCells.com); DOI:10.1634/stemcells.2007-0417.

Carvalhal A. V., Lima, C., Basto V., Cunha C., Escada P., Cruz P. and H. Cruz (2007). Adult human neuronal stem/progenitor cells from the olfactory epithelium and olfactory lamina propria, isolation method, proliferation and differentiation in serum free culture medium and utilization for transplantation. WO2007020611.

Claes L., Eckert-Hubner K. and P. Augat (2002). The effect of mechanical stability on local vascularization and tissue differentiation in callus healing. J. Orthop. Res. 20:255-266.

Cullinane D. M., Salisbury K. T., Alkhiary Y., Eisenberg S., Gerstenfield L. and T. A. Einhorn (2003). Effects of local mechanical environment on vertebrate tissue differentiation during repair: does repair recapitulate development? J. Exp. Biol. 206:2459-2471.

Chul-Won H. A., Yoon-Sun Y. and Y. Sung-Eun (2003) Isolation and culture-expansion methods of mesenchymal stem/progenitor cells from umbilical cord blood, and differentiation method of umbilical cord blood-derived mesenchymal stem/progenitor into various mesenchymal tissues. WO 03070922.

Davies J. E., Dolores B., Raúl S., Morris H. and A. D. S. Lickorish (2004). Progenitor cells from Wharton's jelly of human umbilical cord. WO2004072273.

Deryl L. T. and M. L. Weiss (2008). Concise review: Wharton's jelly-derived cells are a primitive stromal cell population. Stem Cells, 26:591-599.

Do M., Jeong H., Choi B., Hunter L., Langley S., Pazmany L. and P. Trayhurn (2006). Inflammatory gene expression patterns revealed by DNA microarray analysis in TNF-α-treated SGBS human adipocytes. Yonsei Medical Journal, Vol. 47, No 5, 729-736.

Gardner T. N., Stoll T., Marks L., Mishra S. and M. K. Tate (2000). The influence of mechanical stimulus on the pattern of tissue differentiation in a long bone fracture—a FEM study. J. Biomech. 33:415-425.

Harris I. R., Messina D. J., Kihm A. and A. Seyda (2006). Postpartum cells derived from umbilical cord tissue, and methods of making and using the same. WO2006/071794.

Hung S.-C., Chen N.-J., Hsieh S.-L., Li H., Ma H.-L. and W.-H. Lo (2002). Isolation and Characterization of Size-Sieved Stem Cells from Human Bone Marrow. Stem Cells 20:249-258

Kadner A., Zund G., Maurus C., Breymann C., Yakarisik S., Kadner G., Turina M. and S. P. Hoerstrup (2004). Human umbilical cord cells for cardiovascular tissue engineering: a comparative study. European Journal of Cardio-Thoracic Surgery 25:635-641.

Kotobuki N., Kawagoe D., Nomura D., Katou Y., Muraki K., Fujimori H., Goto S., Ioku K. and H. Ohgushi (2006). Observation and quantitative analysis of rat bone marrow stromal cells cultured in vitro on newly formed transparent β-tricalcium phosphate. J. Mat. Sci.: Mat. Med. 17:33-41.

Lee O. K., Kuo T. K., Chen W. M., Lee K. D., Hsieh S. L. and T. H. Chen (2004). Isolation of multipontent mesenchymal stem cells from umbilical cord blood. Blood, 103:1669-1675.

Majumdar M. K., Thiede M. A. and J. D. Mosca (1998). Phenotypic and functional comparison of cultures of marrow-derived mesenchymal stem cells (MSCs) and stromal cells. J. Cell Physiol 176:57-66.

Mitchell K. E., Weiss M. L., Mitchell B. M., Martin P., Davis D., Morales L., Helwig B., Beerenstrauch M., Abou-Easa K., Hildreth T. and D. Troyer (2003). Matrix cells from Wharton's jelly form neurons and glia. Stem Cells 21:50-60, 2003.

Nanaev A. K., Kohnen G., Milovanov A. P., Domogatsky S. P. and P. Kaufmann (1997). Stromal differentiation and architecture of the human umbilical cord. Placenta 18:53-64.

Okada A., Shiomi T., Aoki Y. and M. Fujiwara (2005). Phenytoin stimulates chondrogenic differentiation in mouse clonal chondrogenic EC cells, ATDC5. J. Toxicol. Sci., Vol. 30, No 3, 145-156.

Phan T. T. and I. J. Lim (2006). Isolation of stem/progenitor cells from amniotic membrane of umbilical cord. WO2004019357.

Pittenger M. F., Mackay A. M. and C. B. Beck (1999). Multilineage potential of adult human mesenchymal stem cells. Science 284:143-147.

Purchio A. F., Naughton B. A. and J. San Roman (1998). Production of cartilage tissue using cells isolated from Wharton's jelly. WO199801779.

Roisen F. J., Klueber K. M., Lu C. L., Hatcher L. M., Dozier A., Shields C. B. and S. Maguire (2001) Adult human olfactory stem cells. Brain Res. 890:11-22.

Romanov Y. A., Svintsitskaya V. A. and V. N. Smirnov (2003). Searching for alternative sources of postnatal human mesenchymal stem cells: candidate MSC-Ike cells from umbilical cord. Stem Cells 21:105-110.

Seyda A. and A. Gosiewska (2006). Postpartum cells derived from umbilical cord tissue, and methods of making, culturing, and using the same. WO2006101548.

Shih D. T.-B., Lee D.-C., Chen S.-C., Tsai R.-Y., Huang C.-T., Tsai C.-C., Shen E.-Y. and W.-T. Chiu (2005). Isolation and Characterization of Neurogenic Mesenchymal Stem Cells in Human Scalp Tissue. Stem Cells 23:1012-1020.

Shim W. S. N., Jiang S., Wong P., Tan J., Chua Y. L., Tan Y. S., Sin Y. K., Lim C. H., Chua T., Teh M., Liu T. C. and E. Sim (2004). Ex vivo differentiation of human adult bone marrow stem cells into cardiomyocyte-like cells. Biochem. Biophys. Res. Com. 324:481-488.

Wang H. S., Hung S. C., Peng S. T., Huang C. C., Wei H. M., Guo Y. J., Fu Y. S., Lai M. C. and C. C. Chen (2006). Mesenchymal stem cells in the Wharton's jelly of the umbilical cord, Stem Cells 22:1330-1337.

What is claimed is:

1. A method of recovering precursor cells from an umbilical cord, said method comprising:
   a) providing a portion of an umbilical cord from which the amniotic membrane has been removed but from which umbilical cord vessels have not been extracted, and which has not been subjected to maceration nor crushing of tissues in the sub-amniotic, intervascular, and perivascular regions of said portion of umbilical cord;
   b) digesting said portion of umbilical cord in a first flask with an enzymatic digestion solution under conditions for digesting the umbilical cord tissue of said portion of umbilical cord, without digesting said umbilical cord vessels; and
   c) after said digesting step, collecting cells in three isolation phases:
      (i) a first isolation phase comprising collecting cells that adhere to said first flask after standing at least 5 minutes after said digesting step;
      (ii) a second isolation phase comprising collecting cells that adhere to a second flask from a supernatant, said supernatant generated by centrifuging said enzymatic digestion solution after said digesting step and after said first isolation phase; and
      (iii) a third isolation phase comprising collecting cells from the pellet generated by centrifuging said enzymatic digestion solution after said digesting step and after said first isolation phase;
   thereby recovering precursor cells that can demonstrate osteogenic, chondrogenic, adipogenic, cardiomyogenic, and glial/neurogenic differentiation.

2. The method according to claim 1, wherein said umbilical cord is a human umbilical cord.

3. The method according to claim 1, wherein said portion has been cut transversally and/or from which blood clots have been removed.

4. The method according to claim 1, wherein said enzymatic digestion solution comprises collagenase and trypsin.

5. The method according to claim 4, wherein said enzymatic digestion solution comprises 0.0375-0.075% collagenase II (w/v) and 0.125% trypsin (w/v).

6. The method according to claim 1, wherein said first flask has dimensions providing a ratio of about 1:2:2:37 for umbilical cord tissue mass (g) to bottom surface area of said first flask ($cm^2$) to volume of said enzymatic digestion solution (mL) to total volume of said first flask (mL).

7. The method according to claim 1, wherein said digestion step further comprises agitation of about 100 oscillations/minute, in a dry atmosphere.

8. The method according to claim 1, wherein said digestion is performed under conditions that maintain a pH of 6.4 or higher of said enzymatic digestion solution.

9. The method according to claim 1, wherein the digestion is performed for 2-16 hours.

10. The method according to claim 9, wherein the digestion is performed for about 4 hours.

11. The method according to claim 1, wherein said precursor cells collected in phase (i) are collected following a period of standing of 5 to 300 minutes after the end of said digestion.

12. The method according to claim 1, wherein said precursor cells collected in phase (i) are cultured for one round of expansion, before being collected.

13. The method according to claim 12, wherein said precursor cells collected in phase (i) are cultured to confluence during said expansion, before being collected.

14. The method according to claim 1, wherein said precursor cells collected in phase (ii) are cultured for one round of expansion, before being collected.

15. The method according to claim 14, wherein said precursor cells collected in phase (ii) are cultured to confluence during said expansion, before being collected.

16. The method according to claim 1 wherein at least $8 \times 10^5$ precursor cells are recovered per gram of umbilical cord provided.

17. The method according to claim 1 wherein said method allows 100% efficacy in providing precursor cells for each umbilical cord used.

18. The method according to claim 1, further comprising the step of cryopreservation of said recovered precursor cells.

19. The method according to claim 18, wherein the density of said precursor cells after cryopreservation is about $3 \times 10^6$ cells/mL.

* * * * *